(12) United States Patent
Orten

(10) Patent No.: US 7,082,202 B1
(45) Date of Patent: Jul. 25, 2006

(54) SOUND PICKUP SENSOR

(75) Inventor: Birger Orten, Alesund (NO)

(73) Assignee: Vibrotron AS, Vettre (NO)

( * ) Notice: Subject to any disclaimer, the term of this patent is extended or adjusted under 35 U.S.C. 154(b) by 0 days.

(21) Appl. No.: 09/856,569

(22) PCT Filed: Dec. 1, 1999

(86) PCT No.: PCT/NO99/00361

§ 371 (c)(1),
(2), (4) Date: Jun. 11, 2001

(87) PCT Pub. No.: WO00/35348

PCT Pub. Date: Jun. 22, 2000

(30) Foreign Application Priority Data

Dec. 3, 1998 (NO) .................................. 19985642

(51) Int. Cl.
*A61B 7/04* (2006.01)

(52) U.S. Cl. ........................................ 381/67; 181/131

(58) Field of Classification Search .................. 381/67; 181/131; 600/528, 586
See application file for complete search history.

(56) References Cited

U.S. PATENT DOCUMENTS

| 3,573,394 | A | | 4/1971 | Birnbaum |
| 4,672,976 | A | | 6/1987 | Kroll |
| 4,947,859 | A | * | 8/1990 | Brewer et al. ............... 600/528 |
| 4,987,859 | A | | 1/1991 | Vanderzanden |
| 5,913,829 | A | * | 6/1999 | Reeves et al. .............. 600/528 |
| 6,152,879 | A | * | 11/2000 | Mohler ........................ 600/586 |
| 6,295,365 | B1 | * | 9/2001 | Ota ............................. 381/114 |

* cited by examiner

*Primary Examiner*—Brian T. Pendleton
(74) *Attorney, Agent, or Firm*—Ladas & Parry LLP

(57) ABSTRACT

A sensor (10) preferably for use in an electronic stethoscope (15) comprises a substantially cylindrically shaped viscoelastic contact and transfer body (2) engaging tightly a hard back piece (1) and being tightly surrounded by a piezoelectric member, e.g. one or two piezoelectric foils (4, 7) that convert sound pressure to electrical signals.

10 Claims, 2 Drawing Sheets

Figure 3:
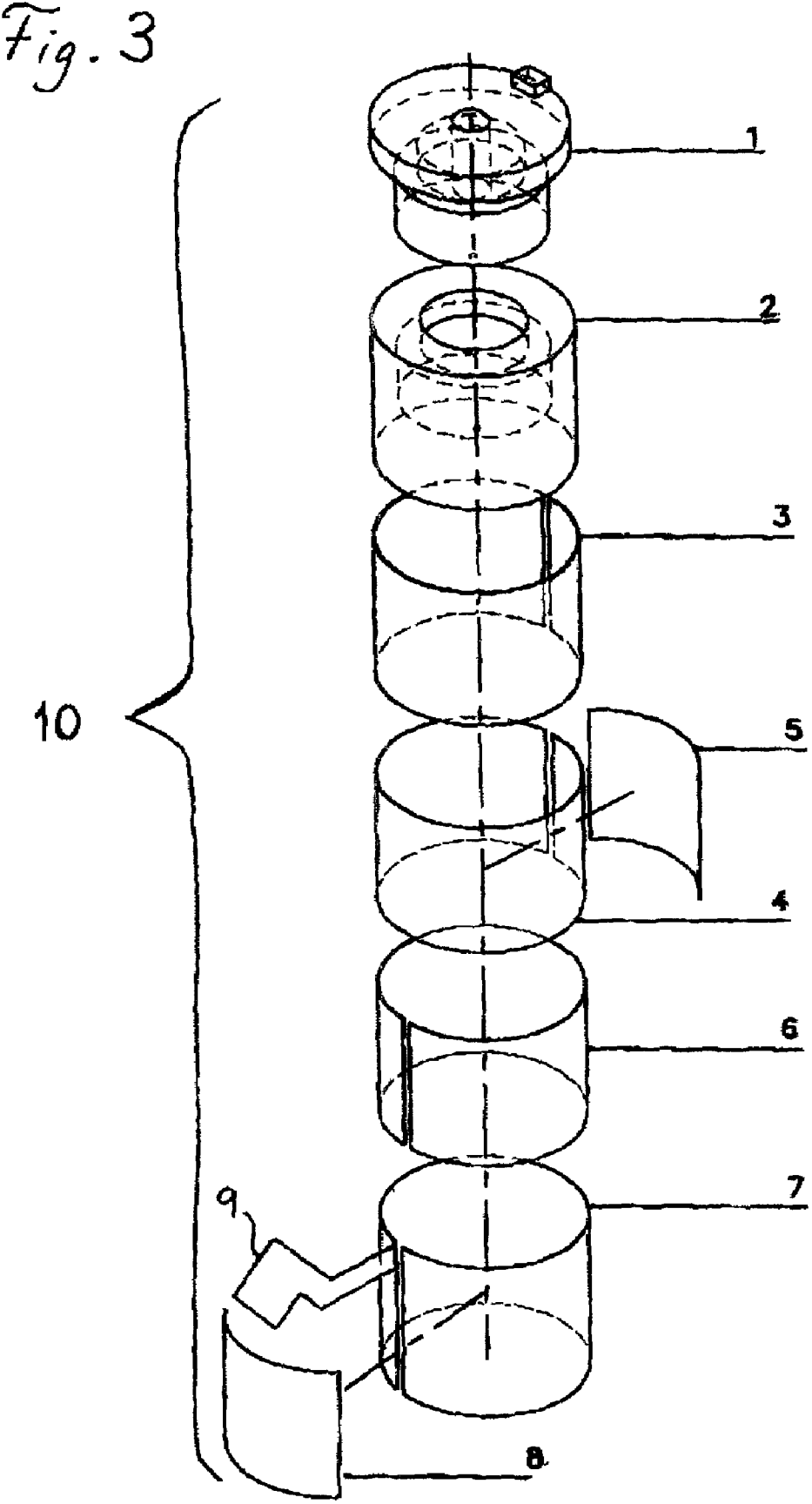

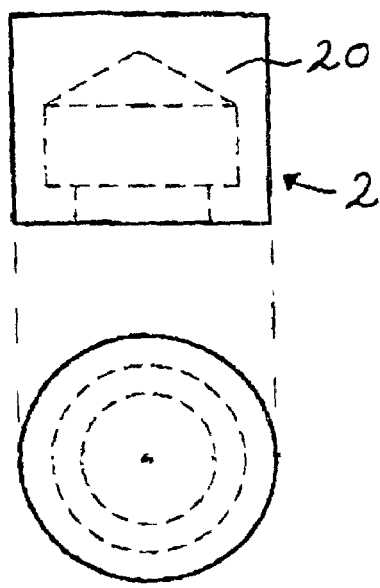
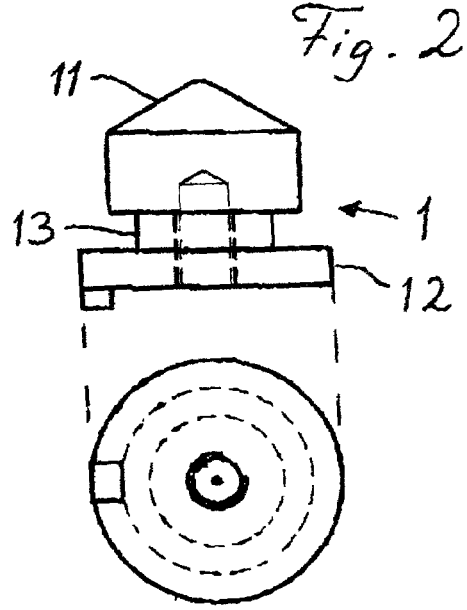
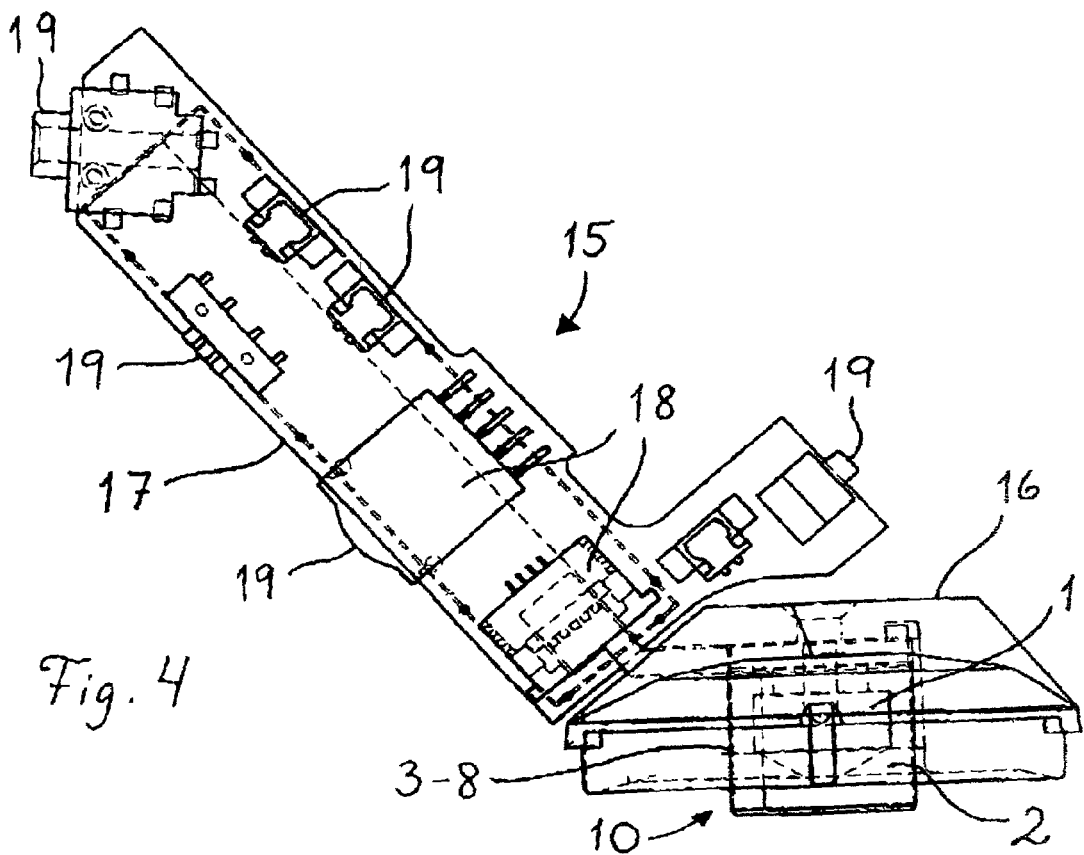

SOUND PICKUP SENSOR

The present invention relates to auscultation, and in particular the invention relates to a sensor for picking up sound generated in an animal or human body, including conversion to an electrical output signal. The invention also relates to a complete electronic stethoscope.

Stethoscopes based on acoustical principles are previously well known and in comprehensive use. Traditional acoustical stethoscopes with supplementary electronic amplification are also previously known. Hydrophones for recording sound from animals under water, are known from biological studies of sea animals. Such techniques constitute a background for the present invention, and these techniques can be considered in the following manner:

Traditional stethoscopes are based on sound carried through the air and through some sort of hose or tube. This is connected with a transmission of sound waves from body tissue to air. Compression of air is sensed in the listener's ears. Sometimes there is a diaphragm in the front end of the apparatus, however there is still a transmission to air. The so-called Littman stethoscopes are examples of this type of technique.

Traditional stethoscopes are sometimes supplemented with microphones picking up the airborne sound in order to amplify it electronically. In this case there is also a transmission of sound from the body tissue to air, and from the air to various types of microphone sensors. Examples of manufacturers of such stethoscopes are Littman and Ariel, and there are also Japanese manufacturers.

The present applicant has previously produced a stethoscope transducer with a pin or peg of a hard material that is brought to direct contact with skin, in such a manner that sound is transferred directly from the body tissue through the hard peg material and into the sensor.

Further, hydrophones for picking up sound in water from animals, ground formations and machine constructions, are well known. Such hydrophones cannot be used for diagnostic purposes in connection with humans and animals, neither inside nor outside a living body.

Ultrasound tools are utilized to a large degree within the field of diagnosis, and these tools often use a type of viscous contact toward the skin. However, the viscous contact is usually constituted by a type of gel, i.e. a gel that does not constitute part of the tool itself, however a gel that is applied to e.g. the skin prior to placing the tool in toward the skin.

From U.S. Pat. No. 4,672,976 in the name Kroll, there is previously known a means for listening for heart sounds, adapted to be placed on the body of a patient, and for detecting low frequency sound waves. This means is equipped with a flexible diaphragm for direct contact to the skin and to adapt to the body contours. A fluid fills an inside volume in the housing of the means, and inside the fluid there is a hydrophone unit. The point of the Kroll means is to provide a good coupling all the way into the hydrophone by minimizing acoustical differences between the body tissue and the materials in the listening means. It is also stated to be an important point that the fluid that surrounds the hydrophone, is a bubble-free, liquid medium or a "hydrophonic gel".

The same Kroll is also a co-inventor in U.S. Pat. No. 4,947,859, in the name Brewer et al, in which patent the same idea as mentioned above, is elaborated further. In U.S. Pat. No. 4,947,859 the sound transducer is developed further, a polymer material is used instead of a liquid solution or gel around a centrally arranged sensor unit in a device similar to a "puck", which device can be placed resting on the skin of a patient. The polymer material is substantially acoustically adapted to the body tissue. The two patents show clearly that it is previously known to utilize an adaptation material intended to imitate the body tissue with regard to acoustical characteristics. However, it is noted that the adaptation does not go further than that. The sensor unit imbedded in the bulk polymer will for instance be influenced by sound from everywhere, and it will not have any directivity or amplification ability. The listening means of Brewer et al is so soft that it can be shaped after the body where it is desirable. This is not an advantage in any connection, in some cases there is a point to having e.g. a rigid diaphragm in close engagement with the skin. Brewer et al are dependent on making signal processing outside "the puck" and the listening device construction provides no screening against inward radiated electrical noise.

The present invention has been conceived to eliminate or alleviate the disadvantages burdening the prior art, such as explained above. Thus, in accordance with the invention there is provided in a first aspect of the invention, a sensor for picking up sound from a body, comprising an acoustoelectric transducer member for converting sound vibrations to electrical output signals, and a viscoelastic unit arranged as an adaptation medium between a body surface and the transducer member, and in such a manner that a front surface of the visco-elastic unit is arranged to be brought to direct engagement with the body surface. The sensor is characterized in that the acoustoelectric transducer member is constituted by at least one piezoelectric member surrounding tightly the lateral surface of the viscoelastic unit, the viscoelastic unit having a cylindrical outer shape, and that the viscoelastic unit engages tightly in its rear end area a hard back piece.

In one embodiment of the invention, the acoustic transducer member is constituted by two concentrically arranged piezoelectric foils, possibly having an electrically conductive foil therebetween. Such an intermediate electrically conductive foil may be constituted by a double-sided adhesive and electrically conductive tape.

In one embodiment, the piezoelectric foil can be constituted by a flat foil laid around the viscoelastic unit in such a manner that adjacent edges are fixed by an adhesive tape. Alternatively, the piezoelectric foil may have a cylindrical shape, and can be threaded tightly onto the viscoelastic unit.

In an alternative embodiment of the sensor, the acoustic transducer member is constituted by a ceramic ring with a piezoelectric effect.

In a preferred embodiment of the invention, the back piece and the viscoelastic unit have in the rear end area precisely complementary shapes comprising an interface that is substantially conically shaped and pointing in a forward direction.

The sensor defined above, finds a favorable use as a sensor element in an electronic stethoscope.

In another embodiment of the invention there is provided an electronic stethoscope comprising a head set with ear phones having loudspeakers, a hand-held sound pick-up module with a sensor element and electronic amplifier circuitry, as well as a connection lead between the module and the headset, and this electronic stethoscope is characterized in that the sensor element is a sensor such as defined in the most general manner above.

Sounds produced in a natural manner, e.g. in a human body, are pressure variations in tissue that mostly contains water. Sound arises in various organs and their movements, compressions, expansions as well as from fluid streams in the body. These sounds are scattered through the body, and frequencies measured in a certain place will depend both on the sound source and the various attenuation and amplification possibilities found inside the body. The purpose of the viscoelastic sensor in accordance with the invention is to transfer the sound waves from the body and into a built-in sensor element/acoustoelectric transducer unit directly through an acoustical adaptation/transformation medium and to the very transducer member in such a manner that sound pressure is distributed uniformly over the sound receiving area of the transducer member. Besides, it is attempted to minimize attenuation and to achieve as wide a range of audible sounds as possible, into the transducer member.

A design as just mentioned differs clearly from all previously known sensor systems in which sound is transmitted through air, and it differs clearly from contact through a peg, in that the area for sound reception from the body is much larger. The invention is also distinguished from ultrasound type devices that operate with frequencies far beyond what the viscoelastic sensor is able to deal with, and the ultrasound systems utilize a gel in a quite different manner to provide contact against the skin, such as previously mentioned.

The invention also is distinguished from sound transmission in viscous elements such as indicated in the US patents belonging to Kroll/Brewer et al, since critical features of the invention are constituted by very different geometrical features.

It is to be noted that such a viscoelastic sensor differs from hydrophones in the fact that whereas traditional hydrophones receive a sound pressure from its outside, the present viscoelastic sensor operates with an internal transmission medium, so that better possibilities are provided for stethoscopic use, in that a larger area is isolated for sound transmission.

Furthermore, immunity toward external sounds is one of the important ideas that have formed a basis for generating the present invention. In cases of accidents and emergencies it may be difficult for a doctor to make a diagnosis by auscultation, since a lot of external and disturbing sounds may arrive from machines, engines, shouting etc. Due to the high impedance of the viscoelastic sensor, airborne, external sound is attenuated. This helps the doctor in focusing on sounds from the body. Such a feature cannot be found in traditional stethoscopes, or in stethoscopes based on microphones, or having diaphragms in connection with a peg arrangement.

Immunity to an "accelerometer effect" is another novel feature. Isocentrical design of the sensor provides isolation against mechanical vibrations due to handling or operation of the viscoelastic sensor. An acceleration force in a direction causing a voltage response, will also induce an opposite force to the to sensing element and thereby result in a voltage having the opposite polarity, and in this manner the noise signal is attenuated.

Good isolation toward external electromagnetic fields is very important with regard to reduction of noise that may disturb the diagnosis function. This is a feature that is novel for the present viscoelastic sensor, as compared to traditional hydrophones.

In the following, the invention shall be explained in more detail by describing embodiments thereof, and while referring to the appended drawings, where FIG. 1 shows an example of a viscoelastic unit constituting part of a sensor in accordance with the invention, FIG. 2 shows a back piece designed to be adapted to the viscoelastic unit in FIG. 1, FIG. 3 shows an embodiment of a sensor in accordance with the invention, in an exploded view to show clearly the parts included in the sensor, and FIG. 4 shows the same embodiment of the sensor as shown in FIG. 3, mounted into a stethoscope module.

To take a closer look at the specific embodiments, it is first referred to FIG. 1. FIG. 1 shows a compact body 2 having a cylindrical outer shape, in a side view and in a view from above. The cylinder body 2 has an inner bore/cavity with an opening from the bottom side. The shape of the bore/cavity is quite complex mentary to the shape of the top sections of the back piece 1 appearing in FIG. 2, which back piece is to be discussed more thoroughly below. On top the cylinder body 2 ends with a substantially plane or somewhat arcuate surface, which surface is the intended reception surface for sound from a body area. The bulk part of the cylinder body 2 is constituted substantially by a homogenous and viscoelastic material 20, the preferred material 20 being rubber, i.e. the cylinder body 2 may preferably be made of cast rubber, preferably silicone rubber.

In FIG. 2 appears a back piece 1 designed to cooperate with the cylinder body 2. At its bottom/rear end, the hard back piece 1 has a base part 12 in the form of a slab, and protruding upward from the slab a narrowed neck-like part 13 which in its turn supports a heard part having a larger diameter. All these parts/sections of back piece 1 are shaped cylindrically and coaxially, but at the front/top end the head part has the shape of a conical surface 11.

It appears clearly that by forcing the head part with its conical tip 11 into the cavity in the cylinder body 2, the rubber mass 20 will snap in place around the head part and the narrowed part 13, in such a manner that close engagement is achieved for the viscoelastic material 20 against the back piece 1 along all surfaces.

The back piece 1 is preferably made of metal, and constructed as an integral body. The most important quality of the back piece 1 is that it is able to provide a uniform sound pressure to a (so far not mentioned in particular) surrounding acoustoelectric transducer member. This is a reason behind the conical shape of the top/forward part of the back piece. In addition to sound reflecting characteristics, i.e. the fact that the material is hard, it is favorable to have good screening characteristics against electromagnetic radiation in toward the actual transducer member and its signal leads, and it is therefore preferable to manufacture the back piece of metal, at least base part 12.

In FIG. 3 appears, in an exploded view, an example of a design of a sensor part in accordance with the invention. The two top parts 1 and 2 are the parts just mentioned in connection with FIGS. 2 and 1. The next part is a double-sided adhesive tape 3 that is not necessary, but may provide an improved attachment for an external piezoelectric foil 4, in the example shown a rectangular sheet with adapted length, to be laid tightly around adhesive tape 3 or directly onto visco-elastic body 2, and which is held tight together using a piece of adhesive tape 5. The sensor foil 4 constitutes the acoustoelectric transducer member of the sensor, and is normally equipped with thin (not shown) signal leads attached to inside and outside.

The embodiment appearing here is based on the use of two piezoelectric foils, and outside foil 4 there is therefore an electrically conductive tape 6, which is preferably also a double-sided adhesive tape. The conductive tape 6 provides electric contact between the outside of the inner piezoelectric foil 4 and a second piezoelectric foil 7 that is placed outside tape 6. An adhesive tape 8 holds the edges of foil 7 in toward each other, in the same manner as tape 5 across the opening of foil 4.

Reference numeral 9 indicates a symbolized circuit connected to the in- and outside of one of the piezoelectric foils, for collecting and processing signal voltages from the foil. In this example, actually a signal wire should also lead to the inside of foil 4, in order to make use of a signal from both foils 4 and 7.

The piezoelectric foils 4 and 7 that have been shown, appear in the example in FIG. 3 as rectangular "sheets" to be laid round a cylindrical shape. However, it is also possible to use cylindrical foils, which must then be threaded tightly outside the viscoelastic body 2. This operation may be a little difficult.

It should be noted that the invention also accommodates other types of acoustoelectric transducers than piezoelectric foils, and another preferred transducer type is a piezoceramic ring, which is somewhat more rigid than a foil, since it is made from a ceramic material, but operating in accordance with the same principle, i.e. by generating a voltage difference between in- and outside when there is a pressure influence from the inside.

In FIG. 4 appears a section through a stethoscope sensor module 15, which is the hand-held instrument used by a doctor for sensing directly from the skin or tissue surface of a patient. A sensor part 10 of the type appearing exploded in FIG. 3, is a central part mounted inside the sensor housing 16 of the sensor module, in such a manner that the forward, substantially flat surface of the viscoelastic body 2 can be made to engage e.g. the skin surface to pick up sound pressure variations. Reference numeral 17 refers to a hand grip part or a main body for sensor module 15, numeral 18 refers generally to electronic circuitry for signal processing and amplification in the module, while switches and warning lamps are generally indicated by reference numeral 19.

The operating mode of the viscoelastic sensor consists in picking up sound waves from the tissue or skin in front of viscoelastic body 2, whereby sound is transmitted into the viscoelastic/viscous medium 20. In the viscoelastic medium 20, the sound energy creates a variable or dynamic pressure toward the inside of the acoustoelectric transducer member 4, 7, and the pressure results in a mechanical tension (stress) in transducer member 4, 7, which in its turn generates electrical voltage directly. The voltage change then takes place with the same frequency and phase as the sound wave. The alternating voltage generated, is the signal that can be amplified, shaped, filtered and modified in various manners in the electronic circuits 18, in such a manner that it is simple to handle or transfer to other electronic devices.

The present sensor has been described in a form that can be utilized in a stethoscope, for ordinary diagnostic activity on human bodies. The contact area for picking up sound waves from the body can be shaped as desired, by deciding the diameter of the sensor body 2. The diagnostic activity can also be carried out with an embodiment of the invention utilizing a piezoceramic transducer member is having medium to high sensitivity surrounding a viscoelastic silicone material. With small variations in configuration and materials, the same concept can be implemented both for use in stethoscopes and for use in instruments to be placed inside the body. The operating, range of the sensor is in the sound range 20 Hz–22 kHz, with an extension option to a range 0 Hz–30 kHz for special purposes.

What is claimed is:

1. Sensor for picking up sound from a body, comprising an acoustoelectric transducer member for converting sound vibrations to electrical output signals;
   a viscoelastic unit arranged as an adaptation medium between a body surface and the transducer member and in such a manner that a front surface of said unit is arranged to be brought to direct engagement with the body surface;
   wherein said acoustoelectric transducer member is comprised of at least one piezoelectric member tightly surrounding the lateral surface of the viscoelastic unit, said viscoelastic unit having a cylindrical outer shape; and
   the viscoelastic unit engages tightly in its rear end area, a hard back piece.

2. The sensor of claim 1, wherein said acoustic transducer member is comprised of at least one thin piezoelectric foil.

3. The sensor of claim 2, wherein said acoustic transducer member is comprised of two concentrically arranged piezoelectric foils and an electrically conductive foil therebetween.

4. The sensor of claim 3, wherein the intermediate electrically conductive foil is comprised of a double-sided adhesive and electrically conductive tape.

5. The sensor of claim 2, wherein said piezoelectric foil is comprised of a flat foil laid around the viscoelastic unit in such a manner that adjacent edges are fixed by an adhesive tape.

6. The sensor of claim 2, wherein the piezoelectric foil has a cylindrical shape and is threaded tightly onto the viscoelastic unit.

7. The sensor of claim 1, wherein the acoustic transducer member is comprised of a ceramic ring with a piezoelectric effect.

8. The sensor of claim 1, wherein said back piece and said viscoelastic unit in the rear end area have precisely complementary shapes comprising an interface that is substantially conically shaped and pointing in a forward direction.

9. The sensor of claim 1, further comprised of a stethoscope, into which said sensor is mounted.

10. An electronic stethoscope comprising a head set with ear phones having loudspeakers, a hand-held sound pick-up module with a sensor element and electronic amplifier circuitry as well as a connection lead between said module and said headset, wherein
   the sensor element is a sensor for picking up sound from a body, and is comprised of:
      an acoustoelectric transducer member for converting sound vibrations to electric output signals, and
      a viscoelastic unit arranged as an adaptation medium between a body surface and said transducer member and in such a manner that a front surface of said unit is arranged to be brought to direct engagement with the body surface, -said acoustoelectric transducer member being comprised of at least one piezoelectric member surrounding tightly the lateral surface of the viscoelastic unit, said viscoelastic unit having a cylindrical outer shape, and
      said viscoelastic unit tightly engages in its rear end area, a hard back piece.

* * * * *